United States Patent [19]

Schoendorfer et al.

[11] 4,416,654
[45] Nov. 22, 1983

[54] PHERESIS APPARATUS

[75] Inventors: Donald W. Schoendorfer, Brookline; Lee E. Hansen, Wellesley, both of Mass.

[73] Assignee: Haemonetics Corporation, Braintree, Mass.

[21] Appl. No.: 299,194

[22] Filed: Sep. 3, 1981

[51] Int. Cl.³ .............................................. B04B 11/00
[52] U.S. Cl. ...................................... 494/10; 494/27; 494/35; 494/37; 604/6
[58] Field of Search ................... 494/1, 10, 35, 36, 23, 494/27, 29, 37; 604/4, 5, 6, 29

[56] References Cited

U.S. PATENT DOCUMENTS

| 4,185,629 | 1/1980 | Cullis | 494/1 |
| 4,187,979 | 2/1980 | Cullis et al. | 494/1 |
| 4,215,688 | 8/1980 | Terman | 604/5 |
| 4,223,672 | 9/1980 | Terman | 604/5 |

OTHER PUBLICATIONS

"Haemonetics 30 Cell Separator Blood Processor", List No. 5830, Owner's Operating & Maintenance Manual, Mar. 1978.

"The Preparation of Leukocyte-Poor Red Blood Cells: A Comparative Study" by H. T. Meryman et al., Transfusion, May–Jun. 1980.

"A Standardized Technique for Efficient Platelet and Leukocyte Collection Using the Model 30 Blood Processor" by Aisner et al., Transfusion, Sep.–Oct. 1976.

"Haemonetics 102 Cell Washing System", List No. 6906, Owner's Operating and Maintenance Manual, Oct. 1978.

Primary Examiner—Robert W. Jenkins
Attorney, Agent, or Firm—Hamilton, Brook, Smith and Reynolds

[57] ABSTRACT

This invention relates to an improvement in two-port centrifuge bowls in which component yield is enhanced by utilizing the centrifuge bowl for eluttriation, as well as centrifugation. In a particular embodiment, platelet yield is improved by terminating flow of anticoagulated whole blood from the donor to the bowl and pumping low density fluid, preferably plasma, back into the bowl at a relatively high rate to elutriate centrifugally separated cells in the bowl.

18 Claims, 3 Drawing Figures

PHERESIS APPARATUS

DESCRIPTION

FIELD OF THE INVENTION

This invention relates to the field of blood processing and, more specifically, to pheresis apparatus and procedures for separating whole blood into its constituent components.

BACKGROUND OF THE INVENTION

Whole human blood includes at least three types of specialized cells. These are red blood cells, white blood cells, and platelets. All of these cells are suspended in plasma, a complex aqueous solution of proteins and other chemicals.

Until relatively recently, blood transfusions have been given using whole blood. There is, however, growing acceptance within the medical profession for transfusing only those blood components required by a particular patient instead of using a transfusion of whole blood. Transfusing only those blood components necessary preserves the available supply of blood, and in many cases, is better for the patient. Before blood component transfusions can be widely employed, however, satisfactory blood separation techniques and apparatus must evolve.

Plasmapheresis is the process of taking whole blood from a donor and separating the whole blood into a plasma component and a non-plasma component under conditions whereby the plasma component is retained and non-plasma component is returned to the donor.

Thrombocytapheresis is similar, except that whole blood is separated into a platelet component and non-platelet component with the platelet component retained or "harvested" and the non-platelet component returned to the donor.

A particularly useful device for the collection of blood cell components is the Haemonetics ®30 Cell Separator Blood Processor manufactured by Haemonetics Corporation, Braintree, Mass. (hereinafter the Model 30). The Model 30 utilizes a conically-shaped centrifuge bowl similar to the bowl described in U.S. Pat. No. 3,145,713, FIG. 6, now called the Latham Bowl. The bowl is held in a chuck which is attached to a spindle and driven by a motor. The bowl consists of a rotor portion wherein blood component is separated and a stator portion consisting of an input and output port. One side of the input port is connected through a first peristaltic pump to a source of whole blood from a donor and the other side is in fluid communication with a fractionation volume in the rotor. Anticoagulant is mixed with the whole blood prior to entry into the centrifuge bowl.

The rotor is rotated at a fixed speed and various blood fractions are collected at the output port and directed into appropriate containers by diverting the flow through tubing in accordance with the setting of three-way clamp/switches.

Fractionation within the centrifuge is determined by the relative densities of the different cell components being separated and collected. The various cell fractions pass through the outlet port of the centrifuge bowl by progressive displacement from the lower portion of the bowl. The operator is trained to visually observe and assess the boundaries or demarcation lines of different component layers as they approach the outlet port of the centrifuge bowl. When the desired fraction has exited the bowl, the centrifuge is stopped. The flow is then reversed and the uncollected cells, such as packed red blood cells (RBC) are returned to the donor.

As a practical matter, however, the boundary between cell layers separated by centrifugation alone is often indistinct.

Aisner et al. in a paper published in Transfusion Sep-Oct 1976 entitled "A Standard Technique for Efficient Platelet and Leukocyte Collection Using Model 30 Blood Processor" graphically illustrates the problems associated with a visual determination of cell fractionation in the plot of FIG. 1 page 438 (reproduced on a different scale in FIG. 2 on this patent application). The results of the experiments reported in the Aisner et al. paper show that considerable overlap exists between the platelet fractionation, the white blood cell (WBC) fractionation and the red blood cell (RBC) fractionation. The reason for this overlap is that a particular cell population will be distributed over a range of densities. Thus, any attempt to separate cells solely by density, as in a centrifuge process such as the Model 30, is bound to result in a certain degree of overlap.

What this means in practice is that cross-contamination of the isolated cells invariably results from the overlap in the range of cell densities. Cross-contamination limits the degree of purity of the isolated cell fractions and makes recognition very difficult and inaccurate, and non-repeatable by visual observation of an operator or other sensory means.

The result is that a compromise is made in present practice. If RBC-free platelets are being harvested, the process is stopped when the fractionation line from the centrifuge bowl to the platelet bag turns a light pink indicating the presence of RBC. This greatly reduces the platelet yield for each cycle through the bowl but insures a substantially RBC-free collection of platelets.

Alternatively, a high platelet yield can be achieved at the expense of an additional centrifuge process by continuing collection of platelets for a predetermined time interval after the observance of the commencement of a pink fraction. This is called the "red cell technique". In the Model 30, the time interval used is about 60–90 seconds. This increases the platelet yield substantially, but requires a subsequent operation in which the collection bag with platelets and a substantial quantity of RBC and WBC is removed from the system and centrifuged at low speeds (150 g) for about 7 minutes, whereupon the supernatant containing the platelets may be expressed, leaving the RBC and WBC in the bag.

In addition to the added time involved in this procedure, the donor is usually not available after this procedure, so the RBC and WBC can no longer be returned to the donor. Additionally, about 10%–25% of the platelets are lost in the process; and the added centrifuge process involves entry into the platelet bag which, while meant to be aseptic, introduces an added risk of contamination.

A known technique for achieving separation of light particles from heavier particles is the process of elutriation. Elutriation achieves separation by causing fluid flow past the particles. This principle has been applied to a pheresis process by Cullis et al. in U.S. Pat. No. 4,187,979 wherein whole blood is collected from a donor in a whole blood bag and then pumped to a first separation chamber mounted on the rotor of a centrifuge. The first separation chamber consists of a diamond-shaped bag with two sets of inlet and outlet ports.

Each inlet port in a set is located diagonally opposite its outlet port. Blood fluid, rich in plasma and low in WBC and platelets, is allowed to flow from a lower inlet port to an upper outlet port transverse to the flow of whole blood across the separation chamber from a side corner inlet port to a side corner outlet port. According to Cullis et al. (col 7, lines 28–35) "In this way, the plasma flow crossing the whole blood flow will elute the white blood cells and platelets from the whole blood and at the same time, the plasma will wash the red blood cells." While this elutriation process is occurring in the first separation chamber, the WBC and platelets may be separated by centrifugation and sedimentation in second and third separtion chambers.

The Cullis et al. system, requiring as it does a four port primary separation chamber and transverse flow of fluid for elutriation, is not compatible with existing hardware/software, such as the Latham bowl, which has only one inout and output port. Also, Cullis et al. is principally directed to the problem of harvesting only red cells whereas an equally important need exists for a method and apparatus of increasing cell-free platelet yields in existing bowl-type centrifuges without destroying or contaminating RBC and, perhaps more significantly, WBC, which are returned to the donor. Additionally, the collection bags for harvesting components from the primary separation chamber are all mounted on the centrifuge rotor making access difficult and, incidentally, subjecting components in such bags to additional unnecessary centrifugal forces.

SUMMARY OF THE INVENTION

In accordance with the invention, a method and apparatus is provided for increasing the yield in a fixed volume two port centrifugation pheresis bowl by utilizing the bowl, not only for centrifugation, but for high flow elutriation as well and thereby providing improved separation of specific cells and enhanced ability to sense separated cell fractions by human visual or machine electro-optical means. In a particular embodiment, the platelet yield is significantly improved, for a given bowl size, by terminating the flow of anticoagulated whole blood from the donor and pumping low density fluid, preferably plasma, back into the bowl and through the centrifugally separated cells in the bowl to elutriate such cells according to their sedimentation rate. In this manner, a higher yield and purer product results.

The process and apparatus of the invention results in:
(a) higher yield of red cell-free platelets than can be obtained without requiring a secondary spin before use;
(b) non-depletion of "contaminants", such as RBC and WBC, which can be returned to the donor; and
(c) applicability to many types of fractionation other than red cell-free platelets using "off-the-shelf" equipment with minor modification.

DESCRIPTION OF THE PREFERRED EMBODIMENT

Figure 1:
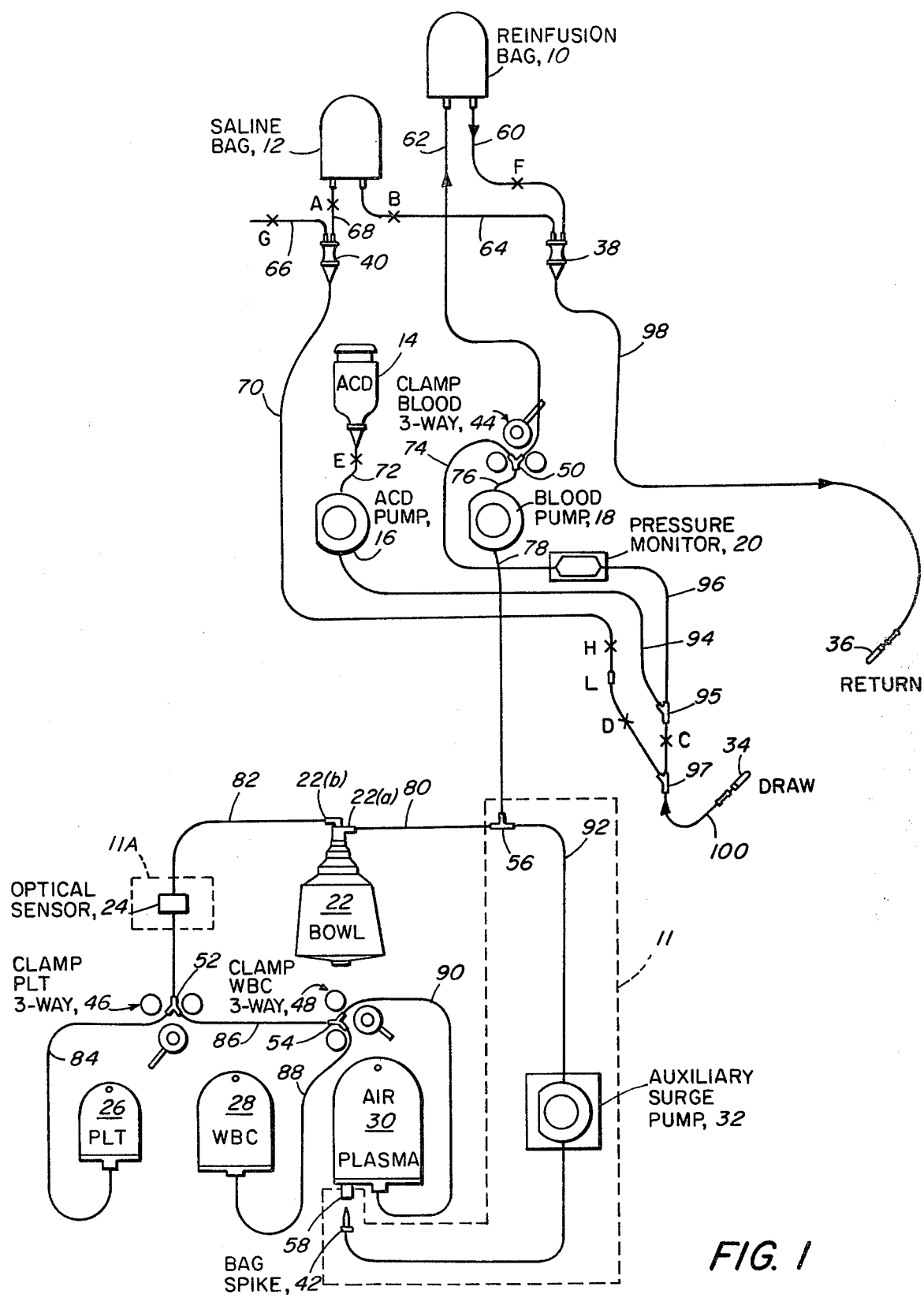
FIG. 1 is a schematic fluid diagram of the pheresis system of the present invention.

Referring now to the drawings in greater detail, there is illustrated schematically in FIG. 1, the apparatus of the present invention. It should be noted that the apparatus shown within the dotted lines and generally designated by reference numerals 11 and 11A, is the modification which is required in order to implement the invention by modifying the Model 30 apparatus, which is the material shown outside the dotted lines.

The material not enclosed in the dotted lines, is extensively described in the *Haemonetics* 30 *Cell Separator Processor Owner's Operating and Maintenance Manual* and, therefore, a detailed and extensive discussion of this material is not required, however, a general description of this apparatus will be included in this specification for ease in reference.

The Model 30 blood processor comprises, in general, a centrifuge bowl 22 of the type described in the previously referenced patent No. 3,145,713 on the Latham bowl. The rotor of the bowl comprises a blood processing chamber and inlet and outlet ports (22(a), 22(b), respectively) are mounted on the centrifuge stator. Two pumps, blood pump 18 and anticoagulant pump 16, and three three-way blood clamps 44, 46 and 48, are provided with the Model 30 blood processor, along with electrical controls (not shown) designed for controlling the pump and clamps for convenience in performing pheresis procedures. A draw needle 34 is provided for withdrawing whole blood by making a venipuncture in the donor. A return phlebotomy needle 36 is provided for making a venipuncture in the donor for returning blood component to the donor. Return phlebotomy needle 36 is connected to drip chamber and filter 38 via plastic tubing 98.

Reinfusion bag 10 is connected via plastic tubing 60 to the opposite side of drip chamber 38 thereby providing fluid communication between the outlet port of reinfusion bag 10 and return phlebotomy needle 36. The inlet port of reinfusion bag 10 is in fluid communication with blood pump 18 via plastic tubing 62 which is coupled to one port of Y-fitment 50 on one side of three-way blood clamp 44. Another part of Y-fitment 50 is coupled to plastic tubing 74 thence through pressure monitor 20, through fitment 95, plastic tubing 100 and ultimately to "draw" phlebotomy needle 34.

Anticoagulant within anticoagulant bottle 14 is coupled through plastic tubing 72 through peristaltic anticoagulant pump 16 and plastic tubing 94 through Y-fitment 95 and plastic tubing 100, to draw phlebotomy needle 34. Similarly, saline bag 12 which is provided with a saline solution, has two outlet ports, one of which is in fluid communication via plastic tubing 64 to the aforementioned drip chamber 38. The other outlet port on saline bag 12 is coupled to an inlet port of drip chamber 40 and thence through plastic tubing 70 to Y-fitment 97 and plastic tubing 100 to draw phlebotomy needle 34. Slide clamps (not shown) are provided at strategic locations labelled A–L. The tubing 66 with a slide clamp located at (G) is provided for a single venipuncture administration set in which the drip chamber and filter 38 is omitted.

Saline bag 12 with a saline solution is provided primarily for priming the system initially in a well-known manner and need not be described further. After the system has been primed and the venipuncture made in the donor in the well-known manner, blood pump 18 is energized along with anitcoagulant pump 16, whereby anticoagulant is continuously mixed with the whole blood drawn from the donor at a constant ratio, inasmuch as the anticoagulant pump and blood pump are interlocked so that they rotate at the same speed. The flow ratio between the two pumps is determined by the size of the pump tubing.

Clamps 44, 46 and 48 are well known three-way clamps which may be manually operated or electronically operated via a solenoid. Three-way clamp 44 is operated when the bowl 22 is being emptied in order to allow a reversal of flow from the bowl via lines 78 and 80 through the pump 18 to tubing 62 and to the reinfusion bag 10. At the same time this flow is reversed, the anticoagulant pump 16 is stopeed so that only the blood pump is reversed. Plastic tubing 82 is coupled at one end to the outlet port of the centrifuge bowl 22 and at the other end to one part of Y-fitment 52 at three-way Latham clamp 46. Depending on the operation of clamp 46, the outlet port of bowl 22 is connected either to the platelet bag 26 via plastic tubing 84 or to one port of Y-fitment 54 at three-way clamp 48. Depending on the position of three-way clamp 48, the conduit 86 may be connected either to white blood cell collection bag 28 via plastic tubing 88 or air/plasma bag 30 via plastic tubing 90.

Bowl 22 is supplied with a volume of sterilized air. Initially, whole blood is drawn from the donor phlebotomy needle 34 through plastic tubing 100, pressure monitor 20, three-way clamp 44, blood pump 18, tubing 80 and into the inlet port of centrifuge bowl 22. Concurrently, anticoagulant from anticoagulant bottle 14 is pumped through condut 72, anticoagulant pump 16, conduit 94 to Y-fitment 95, where it is mixed with the whole blood drawn from phlebotomy needle 34.

The sterile air, initially in the centrifuge bowl 22, is displaced into air/plasma bag 30 via conduit 82, Y-fitment 52 at three-way clamp 46, conduit 86 at three-way clamp 48 and conduit 90 to the inlet port of air/plasma bag 30.

The conduits 84 and 88 to respective bags 28 and 26 are clamped "off" by the operation of three-way clamps 46 and 48. As mentioned previously, these three-way clamps may be operated automatically or manually in a well-known manner.

Anticoagulated whole blood in the centrifuge bowl is now separated into different fractions by the centrifugation process and the first material displaced out of the centrifuge bowl is the plasma, since this is the lightest in density. This plasma is collected in the plasma bag until the buffy coat, which is composed of platelets and white cells, gets to a predetermined location as viewed by the operator at the top of the centrifuge bowl 22. At this point, the operator switches the three-way clamps such that platelet clamp 46 directs the output of the centrifuge bowl via tubing 84 to platelet bag 26. If red cell-free platelets are being harvested in platelet bag 26, the operator is trained to terminate the platelet collection when the effluent from the bowl (viewed in tubing 82 before platelet 3-way clamp 46) is a light pink color, indicating the presence of red cells. At this point, the procedure is stopped and all the contents in the centrifuge bowl 22 and the plasma in the air/plasma bag 30 are pumped to the reinfusion bag 10 for return to the donor by reversing blood pump 18. Also, the air in air plasma bag 30 is returned to the bowl and the bowl 22 is ready for another cycle.

As stated earlier, if a high yield of platelets is desired, this can be obtained by the so-called "red cell technique" wherein platelet collection in bag 26 is allowed to proceed for about an additional period of 60–90 seconds after the demarcation line turns pink. Then the procedure is stopped, the contents of the air/plasma bag 30 are returned to the bowl, the bowl is emptied into the reinfusion bag 10 and then returned to the donor. The whole process is repeated six to eight times, which takes a period of about an hour-and-a-half to two hours. While the end result of the "red cell technique" is an increase in platelet yield in bag 26, the platelets produced are contaminated by a large quantity of red cells, as well as white cells. These platelets, so contaminated, may not be transfused unless ABO cross-matching between the donor and recipient has been performed with satisfactory results, otherwise there is a risk of hemolizing the red cells and causing severe problems with the recipient. The other alternative is to conduct an additional centrifugation of the platelets in the platelet bag in a laboratory-type centrifuge at 150 g's for about 7 minutes in order to separate the platelets from the red cells.

As may be seen from the foregoing description of the present state-of-the-art pheresis process, a need exists for a method of increasing the yield of red cell-free platelets in a manner which avoids additional centrifugation and consequent loss of red cells and/or white cells for reinfusion to the donor. Therefore, in accordance with the invention, we have provided the apparatus, shown in dotted lines in FIG. 1, to provide a simple modification to the existing process which results in the aforementioned desirable properties. The apparatus of the invention comprises an auxiliary surge pump 32, a Y-fitment 56, a bag spike 42, and interconnecting plastic tubing 92 between the bag spike 42 and the Y-fitment 56 and an optional optical sensor 24.

Surge pump 32 is a peristaltic pump substantially identical to blood pump 18 or anticoagulant pump 16. Y-fitment 56 is connected at one port to the input lead to Latham centrifuge bowl 22 and at a second port to the conduit leading to blood pump 18 and at the third port to the additional tubing 92 through peristaltic surge pump 32 and bag spike 42. Bag spike 42 is adapted to be inserted into a secondary inlet port of air/plasma bag 30. In all other respects, the pheresis connections are as previously indicated in FIG. 1.

Anticoagulated whole blood is collected in bowl 22 as previously described, and at a predetermined point the blood pump is turned "off" preventing the introduction of further blood into bowl 22 and the auxiliary pump 32 is turned on at a predetermined flow rate so that plasma from the plasma/air bag 30, which was previously harvested, is recycled through the auxiliary pump 32 via conduit 92 and into the inlet port of Latham bowl 22. The recycled plasma flows through the red cells suspended in the rotor of centrifuge bowl 22 under the influence of the centrifugal force field, and by the process of elutriation separates the heavier cells, the red cells and white cells, from the lighter cells, the platelets. At the same time, the platelet three-way clamp 46 is operated to switch the outlet flow from centrifuge bowl 22 via conduits 82 and 84 to platelet bag 26. As the platelets are forced out of the bowl, eventually the plasma will appear cloudy at the effluent line, as viewed by the operator since the effluent will be very dense with platelets.

After a peak in density is reached, the plasma will begin to clear again, at which time the surge pump is turned off, approximately four seconds after peak density is reached. The blood tubing 100 is then clamped off at point (C) and saline is flushed through the draw needle via drip tube 40. Next, the centrifuge bowl is emptied and the contents reinfused into the donor, in accordance with customary procedure. This process may be repeated for as many passes as desired.

Figure 2:
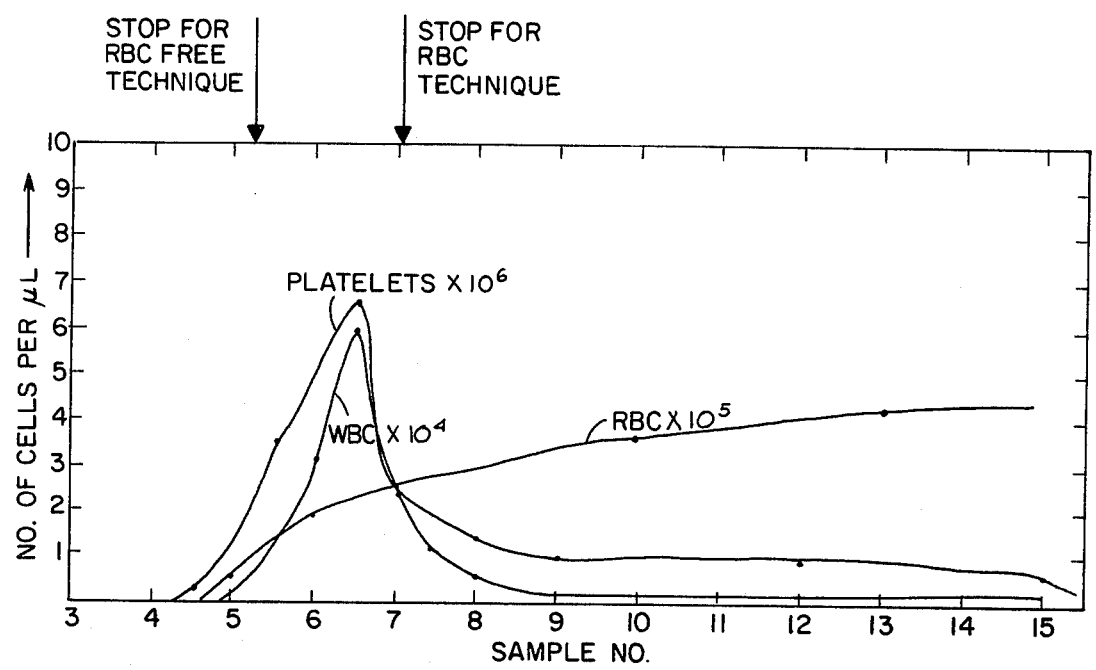
FIG. 2 is a graph, taken from FIG. 1 of the Aisner et al. reference and enlarged in scale, which plots (on the abscissa) the number of various cells collected in a sample versus on the ordinate, the sample number, collected in 15 minute intervals, utilizing a standard Model 30 procedure.
Figure 3:
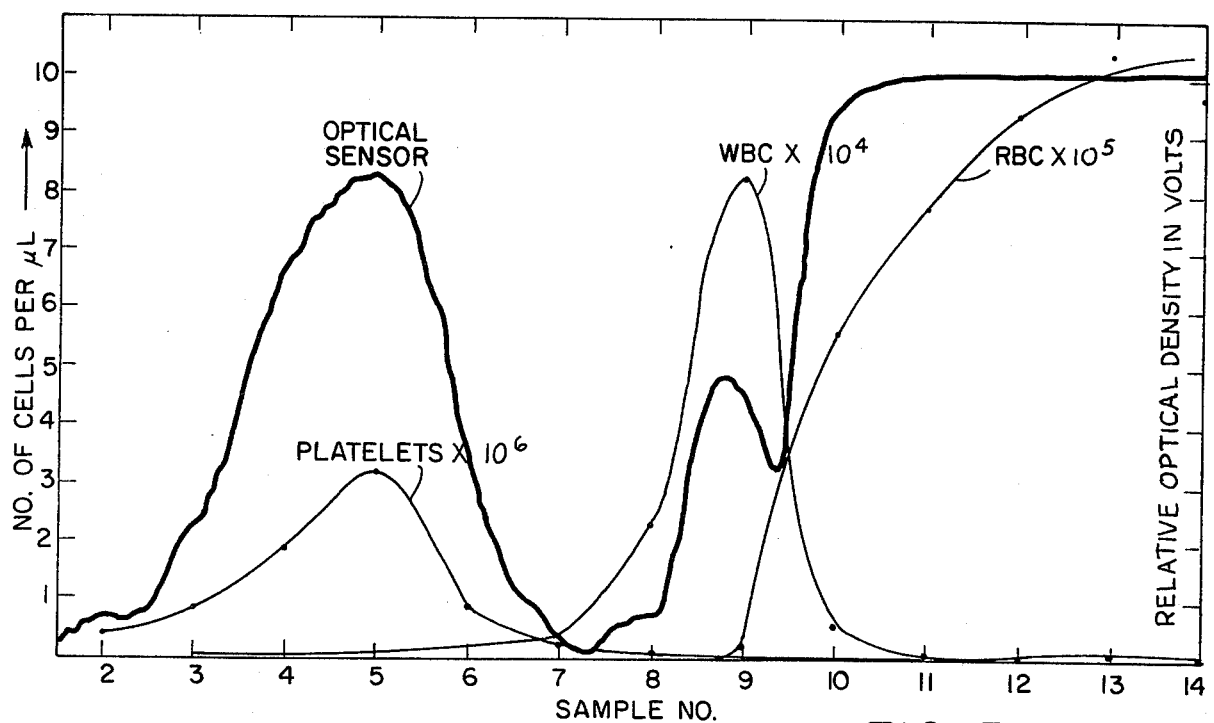
FIG. 3 is a graph as in FIG. 2, utilizing the "surge" technique of the invention with the output voltage of an optical sensor superimposed on the graph.

The end results may be compared by considering the two graphs shown in FIGS. 2 and 3 respectively. FIG. 2 shows a cell separation using a 225 ml bowl in which samples are taken every 15 ml. The data for this figure is taken from the aforementioned paper by Aisner et al. using the prior art Model 30 pheresis procedure. As can be seen in FIG. 2, a substantial overlap exists between the platelet fractionation, the white blood cell fractionation, and the red blood cell fractionation. After the fourth sample, platelets are beginning to be harvested, but then approximately 12 ml after that, white blood cells are also being harvested and also red cells are beginning to pass from the centrifuge to the platelet bag. If substantially red cell-free platelets are desired, without a secondary spin, one would have to stop the process after approximately 20% of the platelets have been harvested. The other alternative is to use the "red cell technique" in which one would continue to harvest the output of the centrifuge for sixty to ninety seconds, whereupon one would obtain substantially more platelets but a good portion of the white cells and many red cells would be harvested along with them.

The graph of FIG. 2 should now be compared with the graph of FIG. 3 which is a plot of the cell separation using a 225 ml bowl with a 200 ml per minute surge through tubing 92 provided in the Model 30 system, in accordance with this invention. As can be seen in FIG. 3, substantially all the platelets have been collected by the seventh sample, while at the same time, very few white blood cells or red blood cells are contained in the sample at this point. This data was gathered by starting surge pump 32 when the buffy coat in the bowl was approximately 1 1/16" from the outer radius of the bowl, as viewed by the operator. At this time, the surge pump 32 is turned on at a rate of 200 ml per minute while the whole blood pump 18 is turned off. The surge pump 32 is allowed to operate for ten to fifteen seconds or until the opacity of the effluent out of the centrifuge clears. Alternatively, an optical sensor 24 may be provided, as shown in FIG. 1, within dotted lines 11A, near the output port of centrifuge bowl 22. Preferably, this optical sensor is adapted to sense, not changes in color per se, but light scattering effects, which are related to the density and size of the particles passing the light sensor. A suitable sensor is the optical switch MCA8 manufactured by General Instruments. Using an optical sensor, the surge pump can be automatically turned off, approximately at the seventh sample point on FIG. 3. A plot of the voltage output of an optical sensor constructed in accordance with the invention, to be sensitive to light scattering, is superimposed on FIG. 3 in heavy lines, from which it can be seen very precise fractions, not only of platelets but also of white blood cells and red blood cells can be achieved utilizing the principles of the invention.

Those skilled in the art will recognize many equivalents to the specific embodiments described herein. For example, the apparatus may be used not only for improving the yield of platelets, but other blood cell components as well. Also, it is contemplated that a single pump could be used as both a surge pump and/or a whole blood pump or ACD pump by modifying the Model 30 circuitry to include switching means which would permit either the whole blood pump or ACD pump to be used as a surge pump. The fluid connection for this modification could be made, for example, at tubing 76. The input and output end of tubing 76 could be connected to two ports of a Y-fitment and the remaining port of the Y-fitment coupled to outlet port 58 or air/plasma bag 30. Accordingly, such equivalents are intended to be a part of this invention and to be covered by the following claims.

I claim:
1. Apparatus comprising:
   (a) a centrifuge;
   (b) an enclosed fractionation volume on said centrifuge;
   (c) an inlet and outlet port mounted on said centrifuge, the ports being in fluid communication with said fractionation volume;
   (d) receptacle means outside said centrifuge for collecting a first fractionated whole blood component from said outlet port;
   (e) pump means for (i) first causing whole blood to flow into said inlet port at a predetermined rate and (ii) secondly for causing a first fractionated component of whole blood to be recirculated to the inlet port of said centrifuge to elutriate the remaining contents in the fractionation volume.

2. The apparatus of claim 1 in which the first fractionated component is plasma.

3. The apparatus of claim 1 in which the pump means is initially deenergized just prior to the point in time when substantial quantity of a blood component being harvested has exited the outlet port and thereafter the pump means is energized to cause said first fractionated component to be recirculated.

4. The apparatus of claim 3 in which the pump means is thereafter deenergized when the majority of the blood component being harvested has exited the outlet port.

5. The apparatus of claim 4 in which opto-electronic means are utilized to determine when the majority of blood component being harvested has exited the outlet port.

6. The apparatus of claim 5 in which the pump means operates at a faster flow rate during elutriation then the rate used when whole blood is caused to flow into the inlet port.

7. The apparatus of claim 5 in which the opto-electronic means responds to light scattering from blood component.

8. The apparatus of claim 1 in which fluid flow during elutriation is substantially parallel to fluid flow during centrifugation.

9. The apparatus of claim 1 in which the centrifuge is a fixed volume bowl and the flow rate during elutriation is substantially greater than during collection.

10. Apparatus for fractionating whole blood into components thereof comprising:
    (a) a centrifuge;
    (b) an enclosed fractionation volume on said centrifuge;

(c) an inlet and outlet port mounted on said centrifuge, the ports being in fluid communication with said fractionation volume;

(d) first pump means for causing whole blood to flow into said inlet port at a predetermined rate;

(e) receptacle means outside said centrifuge for collecting fractionated whole blood component from said outlet port;

(f) second pump means for causing a first fractionated component of said whole blood to be recirculated to the inlet port of said centrifuge to elutriate the remaining contents in the fractionation volume, thereby achieving enhanced separation of component within said centrifuge.

11. The apparatus of claim 10 in which the recirculated component is substantially cell free plasma.

12. The apparatus of claim 10 in which the first pump means is deenergized just prior to the point in time when the platelets, separated from the whole blood, exit the outlet port and the second pump means is energized thereafter.

13. The apparatus of claim 12 in which the second pump is deenergized when the majority of platelets have exited the outlet port, and opto-electronic means are utilized to determine when the majority of platelets have exited.

14. The apparatus of claim 13 in which the opto-electronic means provides an electrical signal proportional to the opacity of material.

15. The apparatus of claim 10 in which the flow rate of the second pump means is at least twice the rate of the first pump means during collection.

16. The method of increasing component yield from donated whole blood in a two-port centrifugation bowl wherein:

(i) lower density component is separated in the bowl from higher density component in the bowl and the lower density component is displaced to a separate container; and (ii) the lower density component is returned to the bowl to elutriate the higher density components remaining in the bowl; and (iii) component with density between lower density component and higher density component is displaced out of the bowl and harvested.

17. The method of claim 16 wherein the components remaining in the bowl after (iii) are reinfused.

18. The method of claim 16 wherein the component is returned in (ii) at a higher flow rate than the rate at which whole blood was pumped into the bowl.

* * * * *